US009451778B2

(12) United States Patent
Rittig et al.

(10) Patent No.: US 9,451,778 B2
(45) Date of Patent: Sep. 27, 2016

(54) ENZYMATIC FLOUR CORRECTION

(75) Inventors: Frank Rittig, Arlesheim (CH); Ramiro Martinez Gutierrez, Madrid (ES); Silvia Strachan, Roschenz (CH); Irina Matveeva, Moscow (RU)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 13/700,923

(22) PCT Filed: Jun. 10, 2011

(86) PCT No.: PCT/EP2011/059703
§ 371 (c)(1),
(2), (4) Date: Apr. 29, 2013

(87) PCT Pub. No.: WO2011/154529
PCT Pub. Date: Dec. 15, 2011

(65) Prior Publication Data
US 2013/0209607 A1    Aug. 15, 2013

Related U.S. Application Data

(60) Provisional application No. 61/354,318, filed on Jun. 14, 2010.

(30) Foreign Application Priority Data

Jun. 11, 2010  (EP) .................... 10165734

(51) Int. Cl.
| | |
|---|---|
| A21D 2/26 | (2006.01) |
| A21D 8/04 | (2006.01) |
| A23L 1/03 | (2006.01) |
| A23L 1/105 | (2006.01) |
| C12N 9/30 | (2006.01) |
| C12N 9/34 | (2006.01) |

(52) U.S. Cl.
CPC ............... *A21D 2/26* (2013.01); *A21D 8/042* (2013.01); *A23L 1/034* (2013.01); *A23L 1/1055* (2013.01); *C12N 9/242* (2013.01); *C12N 9/2428* (2013.01)

(58) Field of Classification Search
CPC ...... A21D 2/26; A23L 1/1055; C12N 9/242; C12N 9/2428
USPC .............................. 426/18, 44, 52
See application file for complete search history.

(56) References Cited

U.S. PATENT DOCUMENTS

| | | |
|---|---|---|
| 4,953,401 A | 9/1990 | Perten |
| 4,990,343 A | 2/1991 | Haarasilta |
| 5,176,927 A | 1/1993 | Haarasilta |
| 5,352,473 A | 10/1994 | Chiqurupati |
| 5,547,690 A | 8/1996 | Vaisanen |
| 5,833,977 A | 11/1998 | Relander |
| 6,250,147 B1 | 6/2001 | Perten |
| 6,548,091 B2 | 4/2003 | Bohlin |
| 6,635,811 B1 | 10/2003 | Flintham et al. |
| 7,018,805 B2 | 3/2006 | Cohen |
| 7,074,579 B1 | 7/2006 | Skerritt |

FOREIGN PATENT DOCUMENTS

| | | |
|---|---|---|
| EP | 0 528 612 A2 | 2/1993 |
| EP | 0 913 092 A2 | 5/1999 |
| JP | 042 07144 | 7/1992 |
| WO | 2005/003311 A2 | 1/2005 |

OTHER PUBLICATIONS

MacArthur, L. A. et al. 1981. Farm Research. 38: 15-18.*
Protein Sequence Search report- Result No. 1. ID AOF63221. (Run on Jan. 13, 2015).*
Biotimes—Correcting flour to perfection with the right partnership.
Mares et al., J Cereal Science, vol. 47, pp. 6-17 (2008).
Mathewson et al., J Food Science, vol. 43, pp. 652-653 (1978).
Popper et al., Enzymes, pp. 229-238 (2007).
Sun et al., Appl Biochem Biotechnol, vol. 160, pp. 988-1003 (2010).
Valjakka et al., Cereal Chem, vol. 71, No. 2, pp. 139-144 (1994).
Novozymes Fungamyl 2500 SG pp. 1-3 (2010).
Novozymes 4000 SG p. 1 (2010).
Novozymes Fungamyl Ultra BG p. 1 (2010).

* cited by examiner

*Primary Examiner* — Hamid R Badr
(74) *Attorney, Agent, or Firm* — Kristin McNamara

(57) ABSTRACT

The present invention is directed to methods for improving flour quality (e.g., a flour correction process) by treating flour with a raw starch degrading enzyme.

14 Claims, No Drawings

ENZYMATIC FLOUR CORRECTION

CROSS-REFERENCE TO RELATED APPLICATIONS

This application is a 35 U.S.C. 371 national application of PCT/EP2011/059703 filed Jun. 10, 2011, which claims priority or the benefit under 35 U.S.C. 119 of European application no. 10165734.4 filed Jun. 11, 2010 and U.S. provisional application No. 61/354,318 filed Jun. 14, 2010, the contents of which are fully incorporated herein by reference.

FIELD OF THE INVENTION

The present invention relates to enzymatic flour correction methods, flour improver compositions, baked good improver methods and baked good improver compositions.

BACKGROUND

A challenge in the baking industry is to secure consistent baked goods (e.g., bread) quality regardless of the quality of the flour used. Flour quality can vary depending on the grain harvested due to variety of factors, such as, the climate and/or soil. Flour quality is standardized (i.e., quality is evaluated and/or improved) by at least two distinct locations in the process stream of converting harvested grain into flour and then into a flour based product (e.g., bread). First, flour is initially standardized at the flour mills/flour improvers following the process of converting grain into flour in a process called flour correction. Second, flour received directly or indirectly from the flour mills/flour improvers is then improved/specialized by the bread improvers/bakery. The quality of flour desired by the flour mills/flour improvers as compared to the bread improvers/bakeries varies significantly. On the one hand, a flour mill/flour improver aims to produce a minimum "standard" flour suitable for trading the flour in the market. By comparison, the bread improvers/bakery prepare more "specialized," high quality flours for direct production of the flour based baked products, often adding additional "bread improvers" (e.g., enzymes, malt flour, and flavor/coloring agents). In addition, highly specialized flour compositions may be prepared to give the desired end product (e.g., bread, baguette, bun, rolls, pizza crust, pretzel, multigrain, dark grain, cake.) the specific qualities desirable or unique to such end product (e.g., color, texture, flavor.).

The quality of flour is generally evaluated at the flour mills by the protein content, the moisture and the ash content of the flour as standard parameters. However, in addition to these standard parameters, the quality of flour is also often evaluated by the "falling number" (FN) of the flour or a similar parameters, e.g. peak viscosity of amylogram, which measures the alpha-amylase activity present in the flour. The falling number is measured using a starch viscosity assay and has an inverse relationship with the alpha-amylase activity present in the grain or flour. Thus, the higher the alpha-amylase activity, the lower the falling number, and vice-versa.

The falling number method and similar assays are used to assess flour quality because a certain amount of alpha-amylase is necessary in flour to provide the fermentation rate in order to obtain good baking results. The alpha-amylase present in flour breaks down the starch in the flour to provide dectrins and finally maltose which is fermentable sugar necessary for the yeast fermentation process used in baking.

The amount of alpha-amylase activity in the flour can have a direct impact on the quality of bread produced. Thus, when the alpha-amylase activity is optimal, a high volume bread with a good texture and crumb structure, bright crust colure, enhanced flavor will result. However, if the alpha-amylase activity is too high, a sticky and wet bread crumb and low volume will result. Conversely, if the alpha-amylase activity is too low, the flour absorbs less water, and a dry bread crumb with a low volume will result.

Poor quality flour is often corrected by the flour mills/flour improvers and/or by bread improvers/bakery. For example, poor quality flour may be corrected by blending grain lots having different qualities to obtain a desired flour quality in the blend, e.g., blending flours having different falling numbers to achieve the desired falling number in the blend. Flours with too high value of a falling number are also often corrected by the supplementation of the flour with malted flour or malt. Malt flour supplementation, however, has significant disadvantages, including, e.g., difficulty in obtaining consistent results (e.g., due to dosing variation and standardization issues), difficulty in handling the malt flour, potential contamination of the malt flour (such as, by microorganisms and insects) and potential high costs associated with production, storage and/or transportation of malt flour.

The use of exogenous grain enzymes (i.e., enzymes not naturally (endogenous) present in the flour grain), have also been used to correct flour. Examples of such enzymes include fungal alpha-amylases, such as the FUNGAMYL products available from Novozymes NS and BAKEZYME P 300 BG product available from DSM. Although avoiding many of the downsides of malt flour supplementation or mixing of grain lots, enzymes have also experienced a number of drawbacks in the industry, e.g., enzymes have not been as effective in flour correction as malt flour supplementation when using the falling number parameter for determining flour quality.

Thus, there remains a need in the art to provide improved, consistent flour correction or to meet flour specifications compositions and methods.

SUMMARY OF THE INVENTION

The present invention is directed to enzymatic flour improvement methods and compositions, which provide advantages over the prior art methods for correcting flour in regard to, among other things, providing consistency in effective application dosages, improved high quality flour and flour based products based on exogenous enzymatic treatment, and substantial cost and handling improvements. The flour and/or flour based product improvements are obtained by treating flour with an effective amount of a raw starch degrading enzyme, alone or in combinations with other enzymes or other flour or dough ingredients and additives.

DETAILED DESCRIPTION OF THE INVENTION

As used herein, "flour correction," "flour improvement" or a method of improving the quality of flour collectively generally refers to a method of improving the quality of flour for standardization and/or subsequent use of the flour in preparing dough based products, such as, in baked goods, e.g., bread. The flour may be corrected or improved, e.g., by the flour mill/flour improver, to a desired standard and/or, the flour may then be improved/specialized, e.g., by the bread improver/bakery.

As used herein, improvements in flour based products, which flour based products include, but are not limited to dough (fresh or frozen) used to prepare flour based consumer products, and flour based consumer products, e.g., baked and fried flour based products, e.g., breads, baguettes, buns, rolls, doughnuts, pizza crusts, pretzels, and cakes As used herein, "flour" means any ground cereal grains or the starch component derived from tubers, legumes, grain, or mixtures thereof. The flour can include, but is not limited to, wheat flour, buckwheat flour, potato flour, corn flour, rice flour, oat flour, bean flour, barley flour, tapioca flour, rye flour and mixtures thereof. In one embodiment the flour comprises wheat flour.

Enzymatic Treatment

In an embodiment, the treatment is performed by applying an effective amount of at least one "raw starch degrading enzyme" to flour. As used herein, a "raw starch degrading enzyme" (also known as a "raw starch hydrolyzing enzyme" or "granule starch hydrolyzing enzyme") refers to an enzyme (or in some cases a combination of enzymes) that can directly degrade raw starch granules at a temperature below the gelatinization temperature of starch. The gelatinization temperature of starch can range from 51° C. to 78° C. and the gelatinization initiation temperature (i.e., when the starch begins to gelatinize) can vary from about 51° C. to 68° C. The variation in gelatinization temperature and gelatinization initiation temperature is generally based on the source of the starch, e.g., wheat, corn, barley, rye, and rice starches may have different gelatinization temperature ranges and gelatinization initiation temperatures.

The raw starch degrading enzyme treatment is an "exogenous" treatment, which means that the effective amount of the raw starch degrading enzyme is not naturally present in the grain/flour (i.e., produced from a gene contained in the cells of the grain plant used to prepare the grain/flour), and is instead either added to the flour or alternatively, the genome of the grain plant used to produce the grain/flour is recombinantly modified to include a gene encoding the raw starch degrading enzyme (or enzymes) using standard plant genomic techniques well-known in the art for transforming a plant cells with an exogenous gene or genes and suitable control sequences to direct expression of the enzyme encoded by the gene.

In an embodiment, the raw starch degrading enzyme has a "raw starch degrading index" (RSDI or Ra/Ga) of at least 0.2, such as, at least 0.3, at least, 0.4, at least 0.5, at least 0.6, at least 0.7, at least 0.8, at least 0.9, at least 1, at least 1.1, at least 1.2, at least 1.3, at least 1.4, at least 1.5, at least 1.6, at least 1.7, at least 1.8, at least 1.9, or at least 2. As used herein, the "raw starch degrading index" is the ratio of enzymatic activity to degrade raw starch (Ra) to enzymatic activity to degrade gelatinized starch (Ga) (Ra/Ga) using the "Ra/Ga assay" further described in the "Materials and Methods" section below.

In an embodiment, the raw starch degrading enzyme comprises at least one alpha-amylase (E.C. 3.2.1.1). Raw starch degrading alpha-amylases are well known and may be obtained from any suitable source, e.g., from suitable microorganisms (fungal, bacterial and yeast). The raw starch degrading alpha-amylase may be a wild-type, variant or synthetically prepared alpha-amylase enzyme.

Particular sources of raw starch degrading alpha-amylases include fungal raw starch degrading alpha-amylases, such as, *Aspergillus* raw starch degrading alpha-amylases, including from *Aspergillus oryzae, Aspergillus niger* and *Aspergillus kawachii*. Examples of such raw starch degrading alpha-amylases are described in WO 2005/003311, WO 2006/0692, WO 2006/060289 and WO 2004/080923. Other examples of raw starch degrading alpha-amylases are hybrid alpha-amylase comprising a starch-binding domain (SBD) and an alpha-amylase catalytic domain (CD). A hybrid alpha-amylase may also comprise an alpha-amylase catalytic domain (CD), a starch binding domain (SBD), and a linker connecting the CD and SBD, as is known in the art. In an embodiment the catalytic domain is derived from a strain of *Aspergillus kawachii*. Examples of hybrid alpha-amylases include those described in WO 2005/003311, U.S. Patent Publication no. 2005/0054071 (Novozymes NS), and U.S. Pat. No. 7,326,548 (Novozymes NS). Examples also include those enzymes disclosed in Table 1 to 5 of the examples in U.S. Pat. No. 7,326,548, and in U.S. Patent Publication no. 2005/0054071 (Table 3 on page 15), such as, an *Aspergillus niger* alpha-amylase catalytic domain (CD) with *Aspergillus kawachii* linker and starch binding domain (SBD). Other raw starch degrading alpha-amylases include those disclosed in WO 2004/020499 and WO 2006/069290 and those disclosed in WO 2006/066579 as SEQ ID NO:2 (hybrid *A. niger* alpha-amylase+SBD (CBD)), SEQ ID NO:3, or SEQ ID NO:4 (JA129). Another example of a raw starch degrading alpha-amylase is the hybrid alpha-amylase consisting of *Rhizomucor pusillus* alpha-amylase with *Aspergillus niger* glucoamylase linker and SBD disclosed as V039 in Table 5 in WO 2006/069290 (Novozymes NS). The raw starch degrading alpha-amylases may also be present in truncated forms, as is well known. Other examples of a raw starch degrading alpha-amylases include the alpha-amylase described in WO 2006/069290 (Novozymes NS), including, e.g., the FUNGAMYL variants (e.g., the variant identified as "COO2") and/or hybrid enzymes, e.g., the FUNGAMYL variant alpha-amylase catalytic domain with the linker and SBD (CBD) of the *Athelia rolfsii* glucoamylase.

The raw starch degrading alpha-amylases for use in the present invention also include alpha-amylases having a high degree of sequence identity to the raw starch degrading alpha-amylases described herein. As used herein, amino acid "sequence identity" refers to the relatedness between two amino acid sequences, and for purposes of the present invention, the degree of amino sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends in Genetics 16: 276-277), preferably version 3.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows: (Identical Residues×100)/(Length of Alignment−Total Number of Gaps in Alignment).

In an embodiment, the raw starch degrading alpha-amylase has sequence identity of at least 50%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, to the amino acid sequence of a raw starch degrading alpha-amylases disclosed herein. For example, the raw starch degrading alpha-amylase for use in the present invention includes raw starch degrading alpha-amylases having at least 50%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with the hybrid alpha-amylase disclosed as V039 in Table 5 in WO 2006/069290. In another example, the raw starch degrading alpha-amylase for use in the present invention includes raw starch degrading alpha-amylases having at least 50%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO:1 of U.S. Pat. No. 7,244,597.

In another embodiment, the raw starch degrading enzyme is a maltotriose (DP3) acting alpha-amylase enzyme. A "maltotriose-acting" enzyme is an alpha-amylase that is able to hydrolyze the substrate maltotriose. In an embodiment, the maltotriose acting alpha-amylase is an alpha-amylase that has an activity of at least 5 micromol/min/mg enzyme activity using the "Maltotriose Activity Assay" described in the "Materials and Methods" section below or using a suitable chromatographic assay, such as, HPLC. In another embodiment, the maltotiose acting alpha-amylase is an alpha-amylase that has at least 6, at least 7, at least 8, at least 9, at least 10, at least 11, at least 12, at least 13, at least 14, at least 15, at least 16, at least 17, or at least 18 micromol/min/mg enzyme activity on maltotriose using the "Maltotriose Activity Assay" described in the "Materials and Methods" section below or using a suitable chromatographic assay, such as, HPLC. An example of a maltotriose acting enzyme for use in the present invention is the hybrid alpha-amylase consisting of *Rhizomucor pusillus* alpha-amylase with *Aspergillus niger* glucoamylase linker and SBD disclosed as V039 in Table 5 in WO 2006/069290 (Novozymes NS).

In another embodiment, the raw starch degrading alpha-amylase is able to degrade oligosaccharides to produce maltotriose (DP3) as a hydrolysis product (e.g., measured using an appropriate assay, such as, a suitable chromatographic assay, e.g., HPLC). In another embodiment, the raw starch degrading alpha-amylase is able to degrade oligosaccharides to produce maltose (DP2) as a hydrolysis product (e.g., measured using an appropriate assay, such as, a suitable chromatographic assay, e.g., HPLC.). In another embodiment, the raw starch degrading alpha-amylase is able to degrade oligosaccharides to produce maltose (DP2) and maltotriose (DP3) as hydrolysis products (e.g., measured using an appropriate assay, such as, a suitable chromatographic assay, e.g., HPLC). In another embodiment, the raw starch degrading alpha-amylase is able to degrade oligosaccharides to produce maltotriose (DP3) as the major hydrolysis product, percentage wise based on the hydrolysis products produced (e.g., using an appropriate assay, such as, a suitable chromatographic assay, e.g., HPLC). In another embodiment, the raw starch degrading alpha-amylase is able to degrade oligosaccharides to produce maltose (DP2) as the major hydrolysis product, percentage wise based on the hydrolysis products produced (e.g., measured using an appropriate assay, such as, a suitable chromatographic assay, e.g., HPLC). In yet another embodiment, the raw starch degrading alpha-amylase is able to degrade oligosaccharides to produce maltotriose (DP3) and maltose (DP2) as the major hydrolysis products (as measured, percentage wise compared to total hydrolysis products, e.g., measured using an appropriate assay, such as, a suitable chromatographic assay, e.g., HPLC). In another embodiment, the hydrolysis products above are the hydrolysis products determined within the first 5 minutes of the enzymatic reaction (e.g., measured using an appropriate assay, such as, a suitable chromatographic assay, e.g., HPLC.). In another embodiment, the hydrolysis products above are the hydrolysis products determined within the first 12 minutes of the enzymatic reaction. In another embodiment, the hydrolysis products above are the hydrolysis products determined within the first 30 minutes of the enzymatic reaction. In another embodiment, the hydrolysis products above are the hydrolysis products determined within the first 60 minutes of the enzymatic reaction. In another embodiment, the hydrolysis products above are the hydrolysis products determined within the 5 hours of the enzymatic reaction In yet another embodiment, the raw starch degrading alpha-amylase is an amylase which is able to hydrolyze DP3, DP4, DP5, DP6, and/or DP7, preferably DP3, DP4, DP5, DP6, and DP7. The activity on these substrates can be measured using a suitable chromatographic assay, e.g., HPLC.

In an embodiment, the raw starch degrading enzyme is a thermostable raw starch degrading enzyme. As used herein, "thermostable" means that the raw starch degrading enzyme has at least 70%, or at least 80% residual enzyme activity at temperature of 40° C. as measured using the Thermostability Assay described in the "Materials and Methods." In an embodiment, the raw starch degrading enzyme has at least 60% or at least 70% residual enzyme activity at temperature of 50° C. as measured using the Thermostability Assay described in the "Materials and Methods." In an embodiment, the raw starch degrading enzyme has at least 50% or at least 60% residual enzyme activity at temperature of 60° C. as measured using the Thermostability Assay described in the "Materials and Methods."

In another embodiment, the raw starch degrading enzyme is an "acid stable alpha-amylase." An "acid stable alpha-amylase" is an alpha-amylase which has 60% residual activity at a pH of 3.0 and/or at a pH of 4.0 and/or at a pH of 5.0 and/or at a pH of 5.0, when activity is measured under the "Acid Alpha-Amylase Assay" further described in the "Materials and Methods" section below.

A particular source of a raw starch degrading "acid stable alpha-amylase" is the acid stable alpha-amylase from *Aspergillus niger* disclosed as "AMYA_ASPNG" in the Swissprot/TeEMBL database under the primary accession no. P56271 and described in more detail in WO 89/01969 (Example 3). The *Aspergillus niger* acid stable alpha-amylase is also shown as SEQ ID NO: 1 in WO 2004/080923 (Novozymes NS) which is hereby incorporated by reference. A commercially available acid stable fungal alpha-amylase derived from *Aspergillus niger* is the product SP288 (SEQ ID NO:1 of U.S. Pat. No. 7,244,597) (available from Novozymes NS). Other sources of acid alpha-amylases include those derived from a strain of the genera *Rhizomucor* and *Meripilus*, such as, a strain of *Rhizomucor pusillus* (WO 2004/055178) or *Meripilus giganteus*. In yet another embodiment, the acid stable alpha-amylase is derived from *Aspergillus kawachii* and is disclosed by Kaneko et al. J. Ferment. Bioeng. 81:292-298(1996) "Molecular-cloning and determination of the nucleotide-sequence of a gene encoding an acid-stable alpha-amylase from *Aspergillus kawachii*"; and further as EMBL: #AB008370.

The raw starch degrading enzymes include enzymes having one or more of the above characteristics of the raw starch degrading enzymes, e.g., thermostability, acid stability, maltotriose activity, ability to degrade oligosaccharides to produce maltotriose (DP3) as a hydrolysis product, ability to degrade oligosaccharides to produce maltose (DP2) as a hydrolysis product, and/or ability to degrade oligosaccharides to DP3, DP4, DP5, DP6, and/or DP7, as previously described. These properties may also be used to select other raw starch degrading alpha-amylase which will be well suited for use in the present invention, including alpha-amylases having a high degree of sequence identity (as described above) to the specific examples of raw starch degrading alpha-amylases amino acid sequences identified herein.

In an embodiment, the raw starch degrading enzyme is an alpha-amylase having maltotriose hydrolyzing activity. In another embodiment, the raw starch degrading alpha-amylase having maltotriose hydrolyzing activity is the hybrid alpha-amylase consisting of *Rhizomucor pusillus* alpha-amylase with *Aspergillus niger* glucoamylase linker and SBD disclosed as V039 in Table 5 in WO 2006/069290 (Novozymes NS) and raw starch degrading alpha-amylases having maltotiose activity and at least 50%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with the hybrid alpha-amylase disclosed as V039 in Table 5 in WO 2006/069290.

In another embodiment, the raw starch degrading enzyme is a thermostable alpha-amylase wherein the alpha-amylase has at least 80% residual enzyme activity at temperature of 40° C. as measured using the Thermostability Assay described in the Materials and Methods. In an embodiment, the raw starch degrading enzyme has at least 70% residual enzyme activity at temperature of 50° C. as measured using the Thermostability Assay described in the "Materials and Methods." In an embodiment, the raw starch degrading enzyme has at least 60% residual enzyme activity at temperature of 60° C. as measured using the Thermostability Assay described in the "Materials and Methods."

In another embodiment, the raw starch degrading enzyme is a thermostable alpha-amylase having maltotriose hydrolyzing activity, wherein the alpha-amylase has at least 80% residual enzyme activity at temperature of 40° C. as measured using the Thermostability Assay described in the "Materials and Methods." In an embodiment, the raw starch degrading enzyme has at least 70% residual enzyme activity at temperature of 50° C. as measured using the Thermostability Assay described in the "Materials and Methods." In an embodiment, the raw starch degrading enzyme has at least 60% residual enzyme activity at temperature of 60° C. as measured using the Thermostability Assay described in the "Materials and Methods."

In an embodiment, the raw starch degrading enzyme is a thermostable, acid stable alpha-amylase having maltotriose hydrolyzing activity, wherein the alpha-amylase has at least 80% residual enzyme activity at temperature of 40° C. as measured using the Thermostability Assay described in the "Materials and Methods," and wherein the alpha-amylase has 60% residual activity at a pH of 5.0, when activity is measured under the "Acid Alpha-Amylase Assay" further described in the "Materials and Methods". In an embodiment, the raw starch degrading enzyme has at least 70% residual enzyme activity at temperature of 50° C. as measured using the Thermostability Assay described in the "Materials and Methods." In an embodiment, the raw starch degrading enzyme has at least 60% residual enzyme activity at temperature of 60° C. as measured using the Thermostability Assay described in the "Materials and Methods."

In another embodiment, the raw starch degrading enzyme is an alpha-amylase having a raw starch degrading raw starch degrading index (RSDI) of at least 0.2, such as, at least 0.3, at least, 0.4, at least 0.5, at least 0.6, at least 0.7, at least 0.8, at least 0.9, at least 1, at least 1.1, at least 1.2, at least 1.3, at least 1.4, at least 1.5, at least 1.6, at least 1.7, at least 1.8, at least 1.9, or at least 2.

In another embodiment, the raw starch degrading enzyme is an alpha-amylase having a raw starch degrading raw starch degrading index (RSDI) of at least 0.2, such as, at least 0.3, at least, 0.4, at least 0.5, at least 0.6, at least 0.7, at least 0.8, at least 0.9, at least 1, at least 1.1, at least 1.2, at least 1.3, at least 1.4, at least 1.5, at least 1.6, at least 1.7, at least 1.8, at least 1.9, or at least 2, and having maltotriose hydrolyzing activity.

In an embodiment, the raw starch degrading enzyme is a thermostable alpha-amylase having a raw starch degrading raw starch degrading index (RSDI) of at least 0.2, such as, at least 0.3, at least, 0.4, at least 0.5, at least 0.6, at least 0.7, at least 0.8, at least 0.9, at least 1, at least 1.1, at least 1.2, at least 1.3, at least 1.4, at least 1.5, at least 1.6, at least 1.7, at least 1.8, at least 1.9, or at least 2, and having at least 80% residual enzyme activity at temperature of 40° C. as measured using the Thermostability Assay described in the "Materials and Methods." In an embodiment, the raw starch degrading enzyme has at least 70% residual enzyme activity at temperature of 50° C. as measured using the Thermostability Assay described in the "Materials and Methods." In an embodiment, the raw starch degrading enzyme has at least 60% residual enzyme activity at temperature of 60° C. as measured using the Thermostability Assay described in the "Materials and Methods."

In an embodiment, the raw starch degrading enzyme is a thermostable alpha-amylase having maltotriose hydrolyzing activity, having a raw starch degrading raw starch degrading index (RSDI) of at least 0.2, such as, at least 0.3, at least, 0.4, at least 0.5, at least 0.6, at least 0.7, at least 0.8, at least 0.9, at least 1, at least 1.1, at least 1.2, at least 1.3, at least 1.4, at least 1.5, at least 1.6, at least 1.7, at least 1.8, at least 1.9, or at least 2; and having at least 80% residual enzyme activity at temperature of 40° C. as measured using the Thermostability Assay described in the "Materials and Methods." In an embodiment, the raw starch degrading enzyme has at least 70% residual enzyme activity at temperature of 50° C. as measured using the Thermostability Assay described in the "Materials and Methods." In an embodiment, the raw starch degrading enzyme has at least 60% residual enzyme activity at temperature of 60° C. as measured using the Thermostability Assay described in the "Materials and Methods."

In an embodiment, the raw starch degrading enzyme is a thermostable, acid stable alpha-amylase having a raw starch degrading raw starch degrading index (RSDI) of at least 0.2, such as, at least 0.3, at least, 0.4, at least 0.5, at least 0.6, at least 0.7, at least 0.8, at least 0.9, at least 1, at least 1.1, at least 1.2, at least 1.3, at least 1.4, at least 1.5, at least 1.6, at least 1.7, at least 1.8, at least 1.9, or at least 2; having maltotriose hydrolyzing activity; having at least 80% residual enzyme activity at temperature of 40° C. as measured using the Thermostability Assay described in the "Materials and Methods"; and having at least 60% residual activity at a pH of 5.0, when activity is measured under the "Acid Alpha-Amylase Assay" further described in the "Materials and Methods" section below. In an embodiment, the raw starch degrading enzyme has at least 70% residual enzyme activity at temperature of 50° C. as measured using the Thermostability Assay described in the "Materials and Methods." In an embodiment, the raw starch degrading enzyme has at least 60% residual enzyme activity at temperature of 60° C. as measured using the Thermostability Assay described in the "Materials and Methods."

In a yet another embodiment, the above raw starch degrading enzymes further have the ability to degrade oligosaccharides to produce maltotriose (DP3) as a hydrolysis product, the ability to degrade oligosaccharides to produce maltose (DP2) as a hydrolysis product, and/or ability to degrade oligosaccharides DP3, DP4, DP5, DP6, and/or DP7, as previously described.

In another embodiment, the raw starch degrading enzyme is used in combination with at least one raw starch degrading glucoamylase (EC.3.2.1.3). Raw starch degrading glucoamylases are well known in the art and may be obtained from plants, animals, and microorganisms, such as, fungal, bacterial and yeast. The raw starch degrading glucoamylase may be a wild-type, variant or synthetically prepared enzyme.

Sources of raw starch degrading glucoamylases include glucoamylases obtained from a fungal host, such as, *Aspergillus*, e.g., *A. niger* G1 or G2 glucoamylase (Boel et al. (1984), EMBO J. 3 (5), p. 1097-1102), the *A. awamori* glucoamylase disclosed in WO 84/02921, and the *A. oryzae* glucoamylase (Agric. Biol. Chem. (1991), 55 (4), p. 941-949). Other raw starch degrading glucoamylases include the glucoamylase derived from a strain of *Athelia*, preferably a strain of *Athelia rolfsii* (previously denoted *Corticium rolfsii*) (see U.S. Pat. No. 4,727,026 and (Nagasaka, Y. et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215), *Trichoderma reesei* glucoamylases disclosed as SEQ ID NO: 4 in WO 2006/060062, and the glucoamylase derived from *Humicola grisea* disclosed as SEQ ID NO: 3 in U.S. Ser. No. 10/992,187. Other raw starch degrading glucoamylases include a glucoamylase derived from a strain of *Trametes*, preferably a strain of *Trametes cingulata* disclosed in WO 2006/069289 (which is hereby incorporated by reference). Other raw starch degrading glucoamylases include the glucoamylases disclosed in WO 2005/045018. Specific examples include the hybrid glucoamylase disclosed in Tables 1 and 4 of Example 1 of WO 2005/045018. Bacterial raw starch degrading glucoamylases include glucoamylases from the genus *Clostridium*, in particular *C. thermoamylolyticum* (EP 135, 138), and *C. thermohydrosulfuricum* (WO 86/01831). Other examples of raw starch degrading glucoamylase include those described in WO 92/00381, WO 00/04136 and WO 01/04273 (from Novozymes NS, Denmark).

The glucoamylase for use in the present invention also include glucoamylases having a high degree of sequence identity to the glucoamylase described herein. In an embodiment, the raw starch degrading glucoamylase has sequence identity of at least 50%, at least 60%, at least 65%, at least 70%, at least 75%, at least 80%, at least 85%, at least 90%, at least 95%, at least 96%, at least 97%, at least 98%, or at least 99% to the amino acid sequence of the raw starch degrading glucoamylases described herein. For example, the raw starch degrading glucoamylase can be an enzyme having a degree of amino acid sequence identify of at least 50%, at least 60%, at least 70%, at least 80%, at least 90%, at least 91%, at least 92%, at least 93%, at least 94%, at least 95%, at least 96%, at least 97%, at least 98%, or at least 99% to the *A. niger* G1 or G2 glucoamylase (Boel et al. (1984), EMBO J. 3 (5), p. 1097-1102), the *A. awamori* glucoamylase disclosed in WO 84/02921, or the *A. oryzae* glucoamylase (Agric. Biol. Chem. (1991), 55 (4), p. 941-949).

The raw starch degrading enzyme may also be used in combination with one or more other non-raw starch degrading glucoamylases. Commercial glucoamylases include, e.g., AMG 1100 BG and AMG Conc. BG (available from Novozymes NS).

The raw starch degrading enzyme may also be used in a combination with one or more other alpha-amylase, such as, a fungal alpha-amylase. Commercial fungal alpha-amylase include, e.g., BAKEZYME P 300 (available from DSM) and FUNGAMYL 2500 SG, FUNGAMYL 4000 BG, FUNGAMYL 800 L, FUNGAMYL ULTRA BG and FUNGAMYL ULTRA SG (available from Novozymes NS)

In an embodiment, the present invention provides a method for improving flour comprising treating the flour with an effective amount of at least one raw starch degrading enzyme and at least one non-raw starch degrading alpha-amylase, preferably, a fungal alpha-amylase. A "non-raw starch degrading" enzyme does not have the raw starch degrading enzyme activity described herein.

In an another embodiment, the present invention provides a method for improving flour comprising treating the flour with an effective amount of at least one raw starch degrading enzyme and at least one non-raw starch degrading glucoamylase.

In an embodiment, the present invention provides a method for improving flour comprising treating the flour with an effective amount of at least one raw starch degrading enzyme and at least one non-raw starch degrading alpha-amylase, preferably, a fungal alpha-amylase, and at least one glucoamylase.

Flour Correction/Flour Improvement/Flour Specialization

Flour quality and flour quality improvements may be measured by determining the falling number of the flour. Flour quality and flour quality improvement may also be measured using any other method. Example of other methods, include other methods which are based on the use of a gelatinized water-flour suspension and viscosity evaluation to measure amylase activity, e.g., the amylograph method.

The falling number may be determined using the Hagberg-Perten method, as described in the Materials and Methods section below. See also Hagberg, s., 1960, Cereal Chemistry, 37, 218 and Hagberg, S., Cereal Chemistry, 38, 202-203, Perten, H., 1964, Cereal Chem., 41:127, and Perten, H., 1967, Cereal Sci. Today, 12:516. This method is also standardized by international bodies such as the ICC, AACC, ISO and ASBC in the standards: ICC/No. 107/1 (1968), AACC/No. 56-81B (1972), ISO/No. ISO/DIS 3093 (1974) and ASBC Barley 12-A.

The raw starch degrading enzyme treatment of the present invention may be applied in an amount to reduce the falling number (FN) of the flour by at least 20 FN units, at least 30 FN units, at least 40 FN units, at least 50 FN units, at least 60 FN units, at least 70 FN units, at least 80 FN units, at least 90 FN units, at least 100 FN units, at least 110 FN units, at least 120 FN units, at least 130 FN units, at least 140 FN units, at least 150 FN units, at least 160 FN units, at least 170 FN units, at least 180 FN units, at least 190 FN units, at least 200 FN units, at least 210 FN units, at least 220 FN units, at least 230 FN units, at least 240 FN units, at least 250 FN units, at least 260 FN units, at least 270 FN units, at least 280 FN units, at least 290 FN units, at least 300 FN. In another aspect, the raw starch degrading enzyme treatment of the present invention may be applied in an amount to reduce the falling number (FN) by at least 30 FN units to 100 FN units. The falling number is measured in seconds (FN units).

In another aspect, the raw starch degrading enzyme treatment is applied in an amount effective to obtain a flour having a desired standard falling number of between 100 and 900, between 150 and 500, between 200 and 450, between 200 and 400, between 200 and 300 or between 250 and 300.

In another embodiment, the enzyme treatment of the present invention is applied to a flour having (prior to treatment with a raw starch degrading enzyme according to the present invention) a falling number of at least 350, at least 400, at least 425, at least 450, at least 475, at least 500, at least 550, at least 600, at least 750, or even at least 900, whereby the falling number is subsequently reduced by the enzyme treatment of the present invention.

In an embodiment, the present invention involves a method for improving flour quality comprising, determining the falling number of flour (e.g., by determining the falling number of one or more samples of the flour), and treating the flour with an effective amount of a raw starch degrading enzyme.

As previously discussed, the improvement in flour may be determined by other methods known for assessing flour quality. Examples include other methods which use gelatinized water-flour suspension and/or viscosity evaluation based on enzymatic addition, such as, the amylograph method, which measures the effect of amylases on starch during rising temperatures and is based on measurement of viscosity. The amylase activity of flour is measured in a scale of Brabender Units (BU), 0-1000. The amylase activity of a flour is inversely proportional to its amylograph value and normal alpha-amylase activity corresponds to about 400 to about 600 BU, such as, about 450-550 BU, whereas low alpha-amylase activity corresponds to about 800 to 900 BU. The Amylograph Method is well-known in the art. The Amylograph Method is described, e.g., in AACC International Approved Methods—AACC Method 22-10.01. Measurement of Alpha-Amylase Activity with the Amylograph.

In addition, other non-viscosity based assays may be used to measure amylase activity in flour in assessing flour quality and/or flour improvement, e.g., standard amylase assays, including, the soluble starch/iodine assay, the Phadebas assay, and turbidity assays (e.g., using a grain amylase analyzer).

In an embodiment, the present invention also provides an enzyme treatment that is at least as effective in correcting flour as malt flour supplementation. According to the present invention, malt flour supplementation may be substantially reduced or entirely eliminated by the enzymatic treatment of the present invention. Accordingly, in an embodiment, the present invention is directed to methods for improving flour quality by treating flour with a raw starch degrading enzyme in combination with reduced malt flour supplementation, wherein the amount of malt flour added to the flour is lower than the amount of malt flour which would be necessary to obtain substantially the same quality flour (e.g., as measured by FN number) without the treatment with raw starch degrading enzyme of the present invention. Accordingly, in one embodiment, the present invention is directed to a method of improving flour quality by treating flour with a raw starch degrading enzyme and wherein the flour is treated with malt flour in an amount of less than 100-2000 ppm, such as, 500-1000 ppm. In another embodiment, the present invention is directed to a method of improving flour quality by treating flour with a raw starch degrading enzyme and wherein the flour is treated with no malt flour supplementation.

Alternatively or more preferably, in addition to measuring the effectiveness of the treatment such as, by falling number (FN) of the flour or other viscosity based assay, or other assays, (such as, by amylase activity assays), and/or by the reduction in malt flour supplementation, flour correction/flour improvement may also be determined by measuring the quality of flour based products prepared from the flour treated according to the present invention. Accordingly, an improvement in the flour quality may be measured by comparing one or more properties of dough or flour based products (e.g., baked products, such as bread) prepared from dough made from flour treated according to the present invention as compared to bread prepared under the same conditions but made from dough made from flour which was not treated according to the present invention. The properties which may be particularly measured include, e.g., volume, texture and crumb quality. These properties may be measured using routine methods known in the art.

Improved baking properties can be determined by comparing a baked product prepared using the enzyme treatment of the present invention with a control baked product prepared under the same conditions (e.g., same recipe), but without the enzyme treatment of the present invention and/or compared to the prior art methods.

The raw starch degrading enzymes are added to the flour in an "amount effective" to correct the flour or improve the flour quality or flour based product quality. As used herein, "an effective amount" is a concentration of enzyme or enzymes sufficient for the intended purpose of improving the flour quality or flour based product quality. An effective amount of an enzyme will vary depending on the objective. For example, a flour mill/flour improver will generally use a lower amount of enzymes (typical dosages of 10-100 ppm of the flour (0.001 to 0.01% wt/flour) or preferably 0.2-20 ppm in order to obtain a "standard" flour suitable for trading whereas a bread improver/baker which will generally use a higher amounts of enzyme (typical dosage of 1000 to 100,000 ppm (0.1 to 10% wt/flour) to obtain a higher quality flour.

Effective amounts of raw starch degrading enzymes for use in the present invention can be determined by the skilled artisan. An effective amount of a raw starch degrading alpha-amylase added may be in the range of, e.g., 0.01-10 mg of enzyme protein per kg of flour, e.g. 1-10 mg/kg. In an embodiment, a fungal raw starch degrading acid alpha-amylase is used and added to the dough in an amount of 0.1 to 100 AFAU/kg flour, such as, 1 to 5 AFAU/kg flour, 0.5 to 3 AFAU/kg flour, and 0.3 to 2 AFAU/kg flour.

An effective amount of a raw starch degrading glucoamylase may be in the range of, e.g., 0.01-10 mg of enzyme protein per kg of flour, e.g. 1-10 mg/kg. In an embodiment, the raw starch degrading glucoamylases is added to the flour in an amount of 0.2-70 AGU/kg flour, such as, 1-50 AGU/kg flour (e.g., between 5-40 AGU/kg flour).

Additional Enzyme Treatment

Optionally, one or more additional enzyme(s) may be used together with the enzyme treatment of the present invention to obtain benefits in dough prepared from the flour. The enzymes are added in an amount effective for their desired purpose of improving the flour, dough and/or flour based product.

The additional enzyme may be selected from the group consisting of another amylase, such as, a non-raw starch degrading alpha-amylase or non-raw starch degrading glucoamylase, a maltogenic amylase, amyloglucosidase, a beta-amylase, a cyclodextrin glucanotransferase, a peptidase (e.g., an exopeptidase), a transglutaminase, a lipolytic enzyme (e.g., lipase, phospholipase, and/or galactolipase), a cellulase, a hemicellulase (e.g., a pentosanase, such as, xylanase), a protease, a protein disulfide isomerase (e.g., a protein disulfide isomerase), a glycosyltransferase, a branching enzyme (e.g., 1,4-alpha-glucan branching enzyme), a 4-alpha-glucanotransferase (e.g., dextrin glycosyltransferase), an oxidoreductase (e.g., a peroxidase, a laccase, a glucose oxidase, a pyranose oxidase, a lipoxygenase, an L-amino acid oxidase and a carbohydrate oxidase, or any combination thereof. The additional enzyme may be of any origin, including mammalian and plant, and preferably of microbial (bacterial, yeast or fungal) origin and may be obtained by techniques conventionally used in the art.

In a particular embodiment, the other enzymes are a xylanase (E.C. 3.2.1.8). Xylanases may be derived from any suitable source, including fungal and bacterial organisms, such as *Aspergillus, Disporotrichum, Penicillium, Neurospora, Fusarium* and *Trichoderma*. Commercially available xylanase preparations for use in the present invention include PENTOPAN MONO BG and PENTOPAN 500 BG (available from Novozymes), GRINDAMYL POWER-BAKE (available from Danisco), and BAKEZYME BXP 5000 and BAKEZYME BXP 5001 (available from DSM).

In another particular embodiment, the other enzyme is a maltogenic alpha-amylase, including the maltogenic alpha-amylases described in EP 120 693, WO 06/032281 and WO/9943794. Commercial maltogenic alpha-amylases include NOVAMYL® (Novozymes NS) and OPTICAKE® (Novozymes NS).

In yet another embodiment, the enzyme is a lipolytic enzyme. Commercial lipolytic enzymes include LIPOPAN F (available from Novozymes NS), LIPOPAN XTRA (available from Novozymes NS), PANAMORE GOLDEN (available from DSM) and PANAMORE SPRING (available from DSM).

In yet another embodiment, the additional enzyme is a G4 amylase (e.g., GRINDAMYL™ POWERFresh, available from Danisco).

Enzyme Compositions

The enzyme preparation may be in any suitable form, such as, in the form of a granulate, agglomerated powder or liquid, which enzyme compositions may be prepared by conventional methods well known in the art.

The present invention is also directed to flour correction compositions comprising a raw starch degrading enzyme in combination with flour or in combination with another flour improver, e.g., those selected from the group consisting of ascorbic acid, potassium bromate, potassium iodate, calcium peroxide, ADA, and mixtures thereof, and an emulsifier, such as, DATEM, SSL, polyoxyethylene sorbitan monostearate (typically referred to as Polysorbate 60) and monoglycerides, such as, hydrated monoglycerides, citrylated monoglycerides, and succinylated monoglycerides.

Flour Based Products

The present invention also relates to flour based products produced according to the present invention, such as, flours, dough (fresh or frozen) used to prepare flour based consumer products, and flour based consumer products, e.g., baked products, e.g., breads, baguettes, buns, rolls, pizza crusts, pretzels, and cakes.

EXAMPLES

Materials and Methods

Improved Volume

Improved volume of baked goods may be measured as the volume of the baked good without a tin divided by the mass of the same baked good measured by rape seed displacement method, which is well known in the art. The unit for specific volume is milliliter per gram.

Improved Texture

Improved texture of a baked goods may be measured as described in Bourne M. C. (2002), 2 ed., Food Texture and Viscosity: Concept and Measurement, Academic Press.

Improved Cohesiveness, Springiness and Resiliency

Improved cohesiveness, springiness and resiliency of baked goods may be measured (e.g., using a texture analyzer, as are well known in the art) as follows: Two consecutive deformations of a cylindrical crumb sample (45 mm) performed with a cylindrical probe (100 mm) with a maximum deformation of 50% of the initial height of the product are performed at a deformation speed of 2 mm/second and waiting time between consecutive deformations of 3 seconds. Force is recorded as a function of time. Cohesiveness is calculated as the ratio between the area under the second deformation curve (downwards+upwards) and the area under the first deformation curve (downwards+upwards). Springiness is calculated as the ratio of the height of the decompression of the second deformation to the height of the decompression of the first deformation with 3 seconds waiting time between deformations. Resiliency is calculated as the ratio between the area under the first upward curve and the first downward curve following deformation.

Improved Elasticity

Improved elasticity of a baked good may be measured as follows: Penetration of crumb with a cylindrical probe (25 mm) until a total deformation of 25% of the initial height of the sample, at a deformation speed of 2 mm/second and keeping the target deformation constant during 20 seconds. Force is registered as a function of time. Elasticity is calculated as the ratio (expressed in percent) between the force measured after 20 seconds at constant deformation to the force applied to obtain the target deformation.

Falling Number Method

The falling number is determined by the Hagberg-Perten method (ICC standard 107/1, www.perten.com), as follows:
Sample Preparation: For grain a 300 gram sample is ground in a Laboratory Mill LM 3100 or LM 120 equipped with a 0.8 mm sieve. The large sample is to avoid sampling error. For flour a representative sample is taken.
Weighing: 7.0±0.05 g of whole meal or flour is weighed and put into a Viscometer tube. The flour amount should be moisture corrected by measuring the actual moisture content of the sample.
Dispensing: 25±0.2 ml of distilled water is added to the tube.
Shaking: Sample and water are mixed by vigorously shaking the tube to obtain a homogeneous suspension.
Stirring: The Viscometer tube with the stirrer inserted is put into the boiling water bath and the instrument is started. After 5 seconds the stirring begins automatically.
Measuring: The stirrer is automatically released in its top position after 60 (5+55) seconds and is allowed to fall down under its own weight.
The Falling Number is the total time in seconds from the start of the instrument until the stirrer has fallen a measured distance registered by the instrument.

Raw Starch Degrading (RSDI (Ra/Ga)) Index Assay

A protocol to obtain a raw starch degrading index (Ra/Ga) value of the enzyme is as follows:
1) The assays are performed at a temperature of 40° C.
2) First, the pH profile of the enzyme is obtained on raw starch. The profile is obtained from the plotting of the enzyme activity versus the pH. This optimum pH value is used in the assay.

3) Any type of raw starch may be used, such as, wheat, corn, barley, rice, etc. As would be known in the art, the raw starch used in the assay should be analytical condition, such as, a high quality native (unmodified) starch. A 2% solution of raw starch is used. Alternatively, to obtain the gelatinized starch solution, a solution of raw starch is heated above the gelatinization temperature for at least 60 minutes. In the case of corn, the solution of raw starch is heated to 70° C. for at least 60 minutes.
4) The reaction solution contains the raw or gelatinized starch) and a buffer. The composition of the buffer used in the assay depends on the pH optimum of the enzyme. The buffer composition and concentration (including pH) must be identical for both the raw and gelatinized starch activity measurements.
5) The enzyme concentration used in the assay must be identical for both the raw and gelatinized starch activity measurements.
6) The enzyme activity is measured by determining the amount of reducing sugars in solution. Suitable methods are the following: The method of Bernfield for determining reducing sugars using dinitrosalicylic acid is described in Bernfield P., Methods Enzymology 1, 149-158 (1955) and the method for determining reducing sugars with copper-bicinchoninate as described in Fox J. D. et al, Analytical Biochemistry 195, 93-96 (1991) or in Waffenschmidt S. et al, Anal. Biochem. 165, 337-340 (1987). Prior to the determination of reducing sugars, the solutions are boiled for 3 minutes and centrifugated to inactivate the enzyme.
7) The time for incubation to measure the enzyme activities is up to 6 hours.
8) The enzyme activity is expressed as the number reducing sugars produced per hour and per mg of pure active enzyme.
9) The activity on gelatinized starch is measured by measuring the release of glucose (or glucose equivalent based on a standard curve prepared from glucose) produced by the enzyme on a 2% gelatinized starch reaction mixture and the activity on raw starch is measured by measuring the release of glucose (or glucose equivalent based on a standard curve prepared from glucose) produced by the enzyme on a 2% raw starch reaction mixture. The activity is measured by the release of reducing sugars produced in 4 micromol per hour per mg of pure active enzyme.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution, Initially, a blackish-blue color is formed, but during the break-down of the starch the blue color gets weaker and gradually turns into a reddish-brown, which is compared to a colored glass standard.

One KNU is defined as the amount of enzyme which, under standard conditions (i.e., at 37° C.+/−0.05; 0.0003 M Ce; and pH 5.6) dextrinizes 5260 mg starch dry substance Merck Amylum solubile.

Acid Stable Alpha-Amylase Activity

For acid stability, residual activity is determined after incubating the enzyme at 37° C. for 2 hr without or with 1 mM $CaCl_2$ at the desired pH (pH 3.0, 4.0 or 5.0). An acid stable alpha-amylase is one that has the residual enzyme activity with and/or without 1 mM $CaCl_2$. Enzyme activity is determined using soluble starch/iodine assay.

FAU Activity

One Fungal Alpha-Amylase Unit (FAU) is defined as the amount of enzyme, which breaks down 5.26 g starch (Merck Amylum solubile Erg. B.6, Batch 9947275) per hour based upon the following standard conditions:
Substrate Soluble starch
Temperature 37° C.
pH 4.7
Reaction time 7-20 minutes Acid Alpha-amylase Activity (AFAU)

Acid alpha-amylase activity is measured in AFAU (Acid Fungal Alpha-amylase Units), which are determined relative to an enzyme standard.

The standard used is AMG 300 L (from Novozymes ANS, glucoamylase wildtype *Aspergillus niger* G1, also disclosed in Boel et al. (1984), EMBO J. 3 (5), p. 1097-1102) and WO 92/00381). The neutral alpha-amylase in this AMG falls after storage at room temperature for 3 weeks from approx. 1 FAU/mL to below 0.05 FAU/mL.

The acid alpha-amylase activity in this AMG standard is determined in accordance with the following description. In this method, 1 AFAU is defined as the amount of enzyme, which degrades 5.260 mg starch dry matter per hour under standard conditions.

Iodine forms a blue complex with starch but not with its degradation products. The intensity of colour is therefore directly proportional to the concentration of starch. Amylase activity is determined using reverse colorimetry as a reduction in the concentration of starch under specified analytic conditions.

Standard conditions/reaction conditions: (per minute)
Substrate: Starch, approx. 0.17 g/L
Buffer: Citate, approx. 0.03 M
Iodine ($I_2$): 0.03 g/L
$CaCl_2$: 1.85 mM
pH: 2.50±0.05
Incubation temperature: 40° C.
Reaction time: 23 seconds
Wavelength: lambda=590 nm
Enzyme concentration: 0.025 AFAU/mL
Enzyme working range: 0.01-0.04 AFAU/mL
Soluble Starch/Iodine Assay A microplate assay method containing: 10 μl diluted enzyme+70 μl MilliQ water 80 μl starch working solution (final concentration: 0.35 g/l gelatinized amylase starch; 50 mM NaAc, pH 4.0; 0.1 M NaCl; 3 mM CaCl2).

Incubate at 37° C. for 2 min with shaking in the microplate reader 40 μl of freshly prepared iodine working solution (final concentration: 0.2% KI; 0.02% iodine) Further incubate at 37° C. for 1 min without shaking in the microplate reader Read OD 590 nm (before reading shake for 10 s)

Glucoamylase Activity

Glucoamylase activity may be measured in AGI or AGU. Glucoamylase (equivalent to amyloglucosidase) converts starch into glucose. The amount of glucose may be determined by the glucose oxidase method for the activity determination. See the method described in the section 76-11 Starch—Glucoamylase Method with Subsequent Measurement of Glucose with Glucose Oxidase in "Approved methods of the American Association of Cereal Chemists", Vol. 1-2 AACC, from American Association of Cereal Chemists, (2000); ISBN: 1-891127-12-8. One glucoamylase unit (AGI) is the quantity of enzyme which will form 1 micro mole of glucose per minute under the standard conditions of the method.

Glucoamylase Unit (AGU) is defined as the amount of enzyme, which hydrolyzes 1 micromole maltose per minute under the standard conditions 37° C. pH 4.3, substrate: maltose 23.2 mM, buffer: acetate 0.1 M, reaction time 5 minutes. An auto-analyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

Maltotriose Activity Assay

Maltotriose activity may be determined as the enzyme activity at a concentration of 10 mg of maltotriose substrate per ml in 0.1 M citrate buffer at pH 5.0, 37° C. for 30 minutes.

Thermostablity Assay

For temperature stability, the enzyme is incubated at the selected temperatures for 1 hr at pH 4.0 with or without 1 mM CaCl2. The enzyme is considered thermostable if it has the required residual activity with and/or without 1 mM CaCl2. Residual activity is assayed using soluble starch/iodine method.

Example 1

A flour sample (Meneba Pelikaan #Dez08) was tested for falling number and determined to have a falling number of 415 (control). Samples of the flour were then treated with enzyme compositions and compared to malt flour supplementation as a reference. The following compositions were tested: a raw starch degrading enzyme (RSDE-A) (the enzyme composition NZ27254, which is a glucoamylase composition also containing a raw starch degrading alpha-amylase side activity) (available from Novozymes NS), AMG 1100, which is a fungal glucoamylase composition (available from Novozymes NS), and malt flour.

As shown in Table 1 below, the enzyme treatment of the invention including a raw starch degrading alpha-amylase reduced the FN value of the flour significantly and on par with the malt flour treatment. The prior art glucoamylase enzyme composition (AMG 1100) treatment gave only a minor reduction, with a maximum of a 15 unit reduction.

TABLE 1

| Treatment | Dosage | Falling Number | Change relative to control |
|---|---|---|---|
| RSDE-A | 200 AGU/kg flour | 383 | −31 |
| RSDE-A | 400 AGU/kg flour | 357 | −58 |
| RSDE-A | 600 AGU/kg flour | 346 | −69 |
| AMG 1100 | 200 AGU/kg flour | 400 | −15 |
| AMG 1100 | 400 AGU/kg flour | 403 | −12 |
| AMG 1100 | 600 AGU/kg flour | 404 | −10 |
| Malt flour | 200 ppm | 386 | −29 |
| Malt flour | 500 ppm | 360 | −54 |
| Control | N/A | 415 | N/A |

Example 2

Baking trials were performed using the same flour (Meneba Pelikaan #Dez08) to prepare bread and rolls. The flour was corrected as described in Example 1 using the same treatment (RSDE-A vs. AMG 1100 vs. malt flour supplementation) and dosages referenced. Pentopan Mono BG in a dosage of 36 ppm (xylanase available from Novozymes A/S) was added to all flours for baking.

The bread and rolls were prepared as follows:

Bread Type: Open top pan bread (350 g)

Crusty rolls (50 g)

Process: Straight Dough System

Flour: Meneba Pelikaan #Dez08

| Ingredients | Percentage % | Grams |
|---|---|---|
| Flour | 100 | 2000 |
| Water | 60 | 1200 |
| Yeast | 4 | 80 |
| Salt | 2 | 40 |
| Sugar | 1 | 20 |
| Ascorbic-Acid | 0.006 | 0.12 |

All ingredients (straight dough system) were added and mixed. The dough was divided into bread (4×350 g) and rolls (1×1500 g).

Dough was evaluated using the following criteria:

Stickiness was rated on a scale from 0 (less) to 10 (more), using a reference sample assessed at 5.

Softness was rated on a scale from 0 (less) to 10 (more), using a reference sample assessed at 5.

Extensibility was rated on a scale from 0 (low) to 10 (high), using a reference sample assessed at 5.

Elasticity was rated on a scale from 0 (low) to 10 (high), using a reference sample assessed at Bread was proofed for 60 min. and rolls were proofed for 50 mins. at 32°-34 C./80% rH. Bread was baked in an open pan at 230° C. and rolls were baked on a sheet at 225° C. with oven steam.

Bread was evaluated using the following criteria:

Internal crumb was rated on a scale from 0 (open grains with thick round cells) to 10 (uniform with fine, thin elongated cells), using a reference sample assessed at 5.

Volume was measured as the volume of the baked good without a tin divided by the mass of the same baked good measured by rape seed displacement method, which is well known in the art. The unit for specific volume is milliliter per gram. and the % volume index was determined relative to the control assessed to be 100%.

Crust color was measured using LabScan colour measurement.

The dosage of malt flour was very low (200 ppm or 500 ppm) for baking purposes, thus the effects on the dough size, volume or in the overall bread qualities for malt flour was less than what would be obtained with normal baking malt flour additions.

As shown in Table 2 below, all tested dosages of RSDE-A resulted in a softer and stickier dough, along with, higher volumes with improved crumb structure qualities, as compared to AMG 1100. Furthermore, an improved crust color was also observed for RSDE-A, as compared to AMG 1100.

TABLE 2

| Treatment | Dosage | Stickiness | Softness | Extensibility | Elasticity | Volume Bread | Crust color Bread | Volume rolls | Crust color rolls |
|---|---|---|---|---|---|---|---|---|---|
| RSDE-A | 200 AGU/kg flour | 6 | 6.5 | 6 | 4 | 110% | 7 | 113% | 7.25 |
| RSDE-A | 400 AGU/kg flour | 6.5 | 7 | 6.5 | 3.5 | 116% | 7.5 | 116% | 8 |
| RSDE-A | 600 AGU/kg flour | 7.5 | 8 | 6.5 | 3.5 | 118% | 8.25 | 121% | 8.75 |
| AMG 1100 | 200 AGU/kg flour | 5 | 5 | 5 | 5 | 105% | 6 | 104% | 6 |
| AMG 1100 | 400 AGU/kg flour | 5 | 6 | 5 | 5 | 110% | 7.25 | 108% | 7.25 |
| AMG 1100 | 600 AGU/kg flour | 6 | 6 | 5 | 5 | 110% | 7.5 | 109% | 8 |
| Malt flour | 200 ppm | 5 | 5 | 5 | 5 | 102% | 5 | 101% | 5 |
| Malt flour | 500 ppm | 5.5 | 5.5 | 5 | 5 | 100% | 5.25 | 105% | 5.25 |
| Control | N/A | 5 | 5 | 5 | 5 | 100% | 5 | 100% | 5 |

Example 3

A second trial was performed to confirm the results obtained in Example 2, with the exceptions that in addition to the raw starch degrading enzyme used in Example 1, the raw starch degrading enzyme produced using a different production host (RSDE-B) and compared to the raw starch degrading enzyme (RSDE-A) of Example 1. Malt flour dosages were also adjusted to standard baking conditions of 0.5% and 1% for the baking trials. The results are produced below, and illustrate that similar results as reported in Example 1 were obtained for RSDE-A and RSDE-B.

TABLE 3

| Treatment | Dosage | Falling Number | Change relative to control |
|---|---|---|---|
| RSDE-A | 200 AGU/kg flour | 375 | −47 |
| RSDE-A | 400 AGU/kg flour | 347 | −74 |
| RSDE-A | 600 AGU/kg flour | 338 | −83 |
| RSDE-B | 200 AGU/kg flour | 378 | −43 |
| RSDE-B | 400 AGU/kg flour | 345 | −76 |
| RSDE-B | 600 AGU/kg flour | 330 | −91 |
| Malt flour | 200 ppm | 387 | −34 |
| Malt flour | 500 ppm | 348 | −74 |
| Control | N/A | 421 | N/A |

TABLE 4

| Treatment | Dosage | Stickiness | Softness | Extensibility | Elasticity | Volume Bread | Crust color Bread | Volume rolls | Crust color rolls |
|---|---|---|---|---|---|---|---|---|---|
| RSDE-A | 200 AGU/kg flour | 6 | 6 | 5.5 | 4 | 111% | 7 | 119% | 6.75 |
| RSDE-A | 400 AGU/kg flour | 7 | 6.5 | 6 | 4 | 113% | 7.25 | 121% | 7.5 |
| RSDE-A | 600 AGU/kg flour | 7 | 7 | 7 | 3.5 | 115% | 8 | 128% | 8 |
| RSDE-B | NZ27254-new | 6 | 6 | 6 | 4 | 111% | 7 | 119% | 6.75 |
| RSDE-B | NZ27254-new | 7 | 6.5 | 6 | 4 | 113% | 7.25 | 123% | 7.5 |
| RSDE-B | NZ27254-new | 7 | 7 | 6.5 | 3.5 | 116% | 8 | 127% | 8 |
| Malt flour | 0.5% | 6.5 | 6.5 | 6 | 3.5 | 110% | 6.5 | 124% | 6 |
| Malt flour | 1% | 7 | 7 | 6.5 | 3 | 115% | 7 | 130% | 7 |
| Control | N/A | 5 | 5 | 5 | 5 | 100% | 5 | 100% | 5 |

Example 4

A flour sample (Meneba Pelikaan) and two samples from this flour were tested for falling number and determined to have falling numbers of 414 and 397 (average of 406). The flour samples taken were treated with the raw starch degrading enzyme (RSDE-C) (which is the hybrid alpha-amylase consisting of *Rhizomucor pusillus* alpha-amylase with *Aspergillus niger* glucoamylase linker and SBD disclosed as V039 in Table 5 in WO 2006/069290 (Novozymes A/S)) at three different dosages. As illustrated in Table 5 below, the raw starch degrading enzyme (RSDE-C) significantly reduced the falling number of the flour.

TABLE 5

| | Dosage | Falling Number |
|---|---|---|
| Trial 1 | | |
| Control | — | 414 |
| RSDE-C | 10 ppm | 243 |
| RSDE-C | 100 ppm | 165 |
| RSDE-C | 500 ppm | 100 |
| Trial 2 | | |
| Control | — | 397 |
| RSDE-C | 10 ppm | 250 |

TABLE 5-continued

| | Dosage | Falling Number |
|---|---|---|
| RSDE-C | 100 ppm | 174 |
| RSDE-C | 500 ppm | 97 |
| RSDE-C Trial 3 | | |
| Control | — | Not measured (avg. of prior two FN |

TABLE 5-continued

| | Dosage | Falling Number |
|---|---|---|
| | | measurements from the flour source was 406) |
| RSDE-C | 10 ppm | 231 |
| RSDE-C | 100 ppm | 148 |
| RSDE-C | 500 ppm | 101 |

The invention claimed is:

1. A method for improving flour quality, comprising adding an effective amount of a raw starch degrading enzyme to flour to improve the flour quality, wherein the raw starch degrading enzyme has at least 90% sequence identity with the amino acid sequence shown in SEQ ID NO:1.

2. The method of claim 1, wherein the raw starch degrading enzyme further comprises at least one glucoamylase.

3. The method of claim 1, wherein the raw starch degrading enzyme comprises at least one raw starch degrading alpha-amylase and at least one raw starch degrading glucoamylase.

4. The method of claim 1, wherein the flour is or comprises wheat flour, rye flour, buckwheat flour, potato flour, corn flour, rice flour, oat flour, bean flour, barley flour, tapioca, and mixtures thereof.

5. The method of claim 1, wherein the raw starch degrading enzyme is added in an amount of 0.001 to 0.01% wt/flour.

6. The method of claim 1, wherein the raw starch degrading enzyme is added in an amount of 0.1 to 10% wt/flour.

7. The method of claim 1, wherein the raw starch degrading enzyme is applied to the flour in combination with one or more enzymes selected from the group consisting of a non-raw starch degrading alpha-amylase, a non-raw starch degrading glucoamylase, a maltogenic amylase, amyloglucosidase, a beta-amylase, a cyclodextrin glucanotransferase, a peptidase, a transglutaminase, a lipolytic enzyme, a cellulase, a hemicellulase, a protease, a protein disulfide isomerase, a glycosyltransferase, a branching enzyme, a 4-alpha-glucanotransferase, and an oxidoreductase.

8. The method of claim 1, wherein the raw starch degrading enzyme is applied to the flour in combination with a non-raw starch degrading alpha-amylase and/or non-raw starch degrading glucoamylase.

9. The method of claim 1, wherein the raw starch degrading enzyme has at least 95% sequence identity with the amino acid sequence shown in SEQ ID NO:1.

10. The method of claim 1, wherein the raw starch degrading enzyme has at least 96% sequence identity with the amino acid sequence shown in SEQ ID NO:1.

11. The method of claim 1, wherein the raw starch degrading enzyme has at least 97% sequence identity with the amino acid sequence shown in SEQ ID NO:1.

12. The method of claim 1, wherein the raw starch degrading enzyme has at least 98% sequence identity with the amino acid sequence shown in SEQ ID NO:1.

13. The method of claim 1, wherein the raw starch degrading enzyme has at least 99% sequence identity with the amino acid sequence shown in SEQ ID NO:1.

14. The method of claim 1, wherein the raw starch degrading enzyme is added in an amount of 0.2-20 ppm.

\* \* \* \* \*

SEQUENCE LISTING

<160> NUMBER OF SEQ ID NOS: 1

<210> SEQ ID NO 1
<211> LENGTH: 595
<212> TYPE: PRT
<213> ORGANISM: Artificial sequence
<220> FEATURE:
<223> OTHER INFORMATION: Synthetic construct

<400> SEQUENCE: 1

```
Ser Pro Leu Pro Gln Gln Gln Arg Tyr Gly Lys Arg Ala Thr Ser Asp
1               5                   10                  15

Asp Trp Lys Gly Lys Ala Ile Tyr Gln Leu Leu Thr Asp Arg Phe Gly
            20                  25                  30

Arg Ala Asp Asp Ser Thr Ser Asn Cys Ser Asn Leu Ser Asn Tyr Cys
        35                  40                  45

Gly Gly Thr Tyr Glu Gly Ile Thr Lys His Leu Asp Tyr Ile Ser Gly
    50                  55                  60

Met Gly Phe Asp Ala Ile Trp Ile Ser Pro Ile Pro Lys Asn Ser Asp
65                  70                  75                  80

Gly Gly Tyr His Gly Tyr Trp Ala Thr Asp Phe Tyr Gln Leu Asn Ser
                85                  90                  95

Asn Phe Gly Asp Glu Ser Gln Leu Lys Ala Leu Ile Gln Ala Ala His
            100                 105                 110

Glu Arg Asp Met Tyr Val Met Leu Asp Val Val Ala Asn His Ala Gly
        115                 120                 125

Pro Thr Ser Asn Gly Tyr Ser Gly Tyr Thr Phe Gly Asp Ala Ser Leu
    130                 135                 140

Tyr His Pro Lys Cys Thr Ile Asp Tyr Asn Asp Gln Thr Ser Ile Glu
145                 150                 155                 160

Gln Cys Trp Val Ala Asp Glu Leu Pro Asp Ile Asp Thr Glu Asn Ser
                165                 170                 175

Asp Asn Val Ala Ile Leu Asn Asp Ile Val Ser Gly Trp Val Gly Asn
            180                 185                 190

Tyr Ser Phe Asp Gly Ile Arg Ile Asp Thr Val Lys His Ile Arg Lys
        195                 200                 205

Asp Phe Trp Thr Gly Tyr Ala Glu Ala Ala Gly Val Phe Ala Thr Gly
    210                 215                 220

Glu Val Phe Asn Gly Asp Pro Ala Tyr Val Gly Pro Tyr Gln Lys Tyr
225                 230                 235                 240

Leu Pro Ser Leu Ile Asn Tyr Pro Met Tyr Tyr Ala Leu Asn Asp Val
                245                 250                 255

Phe Val Ser Lys Ser Lys Gly Phe Ser Arg Ile Ser Glu Met Leu Gly
            260                 265                 270

Ser Asn Arg Asn Ala Phe Glu Asp Thr Ser Val Leu Thr Thr Phe Val
        275                 280                 285
```

-continued

```
Asp Asn His Asp Asn Pro Arg Phe Leu Asn Ser Gln Ser Asp Lys Ala
        290                 295                 300
Leu Phe Lys Asn Ala Leu Thr Tyr Val Leu Leu Gly Glu Gly Ile Pro
305                 310                 315                 320
Ile Val Tyr Tyr Gly Ser Glu Gln Gly Phe Ser Gly Gly Ala Asp Pro
                325                 330                 335
Ala Asn Arg Glu Val Leu Trp Thr Thr Asn Tyr Asp Thr Ser Ser Asp
            340                 345                 350
Leu Tyr Gln Phe Ile Lys Thr Val Asn Ser Val Arg Met Lys Ser Asn
                355                 360                 365
Lys Ala Val Tyr Met Asp Ile Tyr Val Gly Asp Asn Ala Tyr Ala Phe
        370                 375                 380
Lys His Gly Asp Ala Leu Val Val Leu Asn Asn Tyr Gly Ser Gly Ser
385                 390                 395                 400
Thr Asn Gln Val Ser Phe Ser Val Ser Gly Lys Phe Asp Ser Gly Ala
                405                 410                 415
Ser Leu Met Asp Ile Val Ser Asn Ile Thr Thr Thr Val Ser Ser Asp
            420                 425                 430
Gly Thr Val Thr Phe Asn Leu Lys Asp Gly Leu Pro Ala Ile Phe Thr
        435                 440                 445
Ser Ala Thr Gly Gly Thr Thr Thr Thr Ala Thr Pro Thr Gly Ser Gly
450                 455                 460
Ser Val Thr Ser Thr Ser Lys Thr Thr Ala Thr Ala Ser Lys Thr Ser
465                 470                 475                 480
Thr Ser Thr Ser Ser Thr Ser Cys Thr Thr Pro Thr Ala Val Ala Val
                485                 490                 495
Thr Phe Asp Leu Thr Ala Thr Thr Thr Tyr Gly Glu Asn Ile Tyr Leu
            500                 505                 510
Val Gly Ser Ile Ser Gln Leu Gly Asp Trp Glu Thr Ser Asp Gly Ile
        515                 520                 525
Ala Leu Ser Ala Asp Lys Tyr Thr Ser Ser Asp Pro Leu Trp Tyr Val
        530                 535                 540
Thr Val Thr Leu Pro Ala Gly Glu Ser Phe Glu Tyr Lys Phe Ile Arg
545                 550                 555                 560
Ile Glu Ser Asp Asp Ser Val Glu Trp Glu Ser Asp Pro Asn Arg Glu
                565                 570                 575
Tyr Thr Val Pro Gln Ala Cys Gly Thr Ser Thr Ala Thr Val Thr Asp
            580                 585                 590
Thr Trp Arg
        595
```